United States Patent [19]

Hayashi et al.

[11] Patent Number: 5,415,964
[45] Date of Patent: May 16, 1995

[54] PIGMENT-CONTAINING POLYMER PARTICLES, METHOD OF PRODUCTION THEREOF

[75] Inventors: Kenji Hayashi; Mikio Koyama; Yoshiaki Koizumi; Tomoe Kikuchi, all of Hino, Japan

[73] Assignee: Konica Corporation, Tokyo, Japan

[21] Appl. No.: 196,526

[22] Filed: Feb. 15, 1994

[30] Foreign Application Priority Data

Feb. 15, 1993 [JP] Japan ................................. 5-047142

[51] Int. Cl.$^6$ .......................... G03G 9/08; C08K 9/10; A61K 47/00
[52] U.S. Cl. ................................ 430/106; 430/106.6; 430/137; 524/800; 524/801; 524/802; 523/205; 523/206; 526/909; 424/1.29
[58] Field of Search ................................. 523/205, 206; 524/800-804; 430/106, 106.6, 137; 526/909, 911; 424/1.29

[56] References Cited

U.S. PATENT DOCUMENTS

| | | | |
|---|---|---|---|
| 4,680,200 | 7/1987 | Solc | 526/909 |
| 4,983,488 | 1/1991 | Tan et al. | 524/803 |
| 5,242,964 | 9/1993 | Bibette et al. | 523/206 |

*Primary Examiner*—Tae H. Yoon
*Attorney, Agent, or Firm*—Finnegan, Henderson, Farabow, Garrett & Dunner

[57] ABSTRACT

A method of manufacturing pigment containing polymer particles comprises the steps of dissolving a surface active agent in a water at concentration higher than the CMC, dispersing a pigment, diluting the suspension at the concentration not higher than the CMC, and adding a monomer and a polymerization initiator for forming the pigment-containing polymer particles.

27 Claims, No Drawings

PIGMENT-CONTAINING POLYMER PARTICLES, METHOD OF PRODUCTION THEREOF

FIELD OF THE INVENTION

The present invention relates to pigment-containing polymer particles, a method of production thereof, an electrophotographic toner and an immunological diagnostic reagent carrier.

BACKGROUND OF THE INVENTION

Colorant-containing polymer particles consisting of a complex of a resin (polymer) and a colorant are used as electrophotographic toner particles and immunological diagnostic reagent carriers.

It is preferable that colorant-containing polymer particles used for these applications be as small in particle size as possible; there is a need for the development of colorant-containing polymer particles having a small particle size of about 0.5 μm.

In the field of electrophotographic toners, for instance, toner particle size and shape can easily be controlled, if toner particles are prepared by associating colorant-containing polymer particles of small particle size. The toner particles thus obtained are expected to be smaller in particle size and narrower in particle size distribution than toner particles prepared by so-called the kneading milling method or the like.

In the field of immunological diagnostic reagent carriers, particle size reduction for colorant-containing polymer particles is expected to provide immunological diagnostic reagents of high coagulation speed and high sensitivity.

With these aspects in mind, the present inventors investigated particle size reduction for polymer particles containing pigment particles as a colorant.

In producing pigment-containing polymer particles using inorganic pigment particle, for instance, the following technologies can be applied.

1) Encapsulation polymerization of inorganic pigment on the basis of lower critical consolute temperature [Journal of American Chemical Society, 200, 131 (1984].
2) Encapsulation polymerization of inorganic pigment by emulsification polymerization [journal of Polymer Science: Part A: Polymer Chemistry, Vol. 25, 3117–3125 (1987].

However, complexation of inorganic pigment particles (inorganic substance) and a polymer (organic substance) is difficult due to a lack of hydrophilicity on their surfaces and due to the polymerization stopping action of some inorganic pigment particles. When inorganic pigment particles of small particle size, in particular, are used, comptexation of said inorganic pigment particles and the polymer is very difficult.

Also, with respect to polymer particles containing an organic pigment, particle size reduction is very difficult.

SUMMARY OF THE INVENTION

The present invention has been developed against the above-described background. Accordingly, it is an object of the present invention to provide pigment-containing polymer particles by far smaller in particle size than conventional pigment-containing polymer particles.

It is another object of the present invention to provide a method of efficiently producing such pigment-containing polymer particles of small particle size.

It is still another object of the present invention to provide an electrophotographic toner of excellent properties obtained from such pigment-containing polymer particles of small particle size.

It is yet another object of the present invention to provide an immunological diagnostic reagent carrier of excellent properties obtained from such pigment-containing polymer particles of small particle size.

The pigment-containing polymer particles of the present invention as containing an organic pigment are prepared by polymerization of a monomer composition containing at least one hydrophobic monomer in an aqueous dispersion of organic pigment particles dispersed in the presence of a surfactant, and are characterized in that the concentration of said surfactant at said polymerization is lower than the critical micelle concentration (CMC).

The organic pigment particles dispersed in the aqueous system are preferably coagulated particles having a particle size not greater than 10 times the primary particle size.

The pigment-containing polymer particles of the present invention as containing an organic pigment are prepared by polymerization of a monomer composition containing at least one hydrophobic monomer and 0.1 to 15% by weight of at least one hydrophilic monomer in an aqueous dispersion of organic pigment particles dispersed in the presence of a surfactant, and are characterized in that the concentration of said surfactant at said polymerization is lower than the critical micelle concentration (CMC).

The organic pigment particles dispersed in the aqueous system are preferably coagulated particles having a particle size not greater than 10 times the primary particle size.

The hydrophilic monomer as a component of the monomer composition is preferably at least one monomer selected from the group consisting of monomers containing the carboxyl group, monomers containing the sulfo group, primary amines, secondary amines, tertiary amines and quaternary ammonium salts, all capable of introducing a polar group to the side chain of the polymer.

The method of the present invention of producing pigment-containing polymer particles as containing an organic pigment comprises a pigment dispersion process for preparing a pigment dispersion by dispersing organic pigment particles in the presence of a surfactant at concentrations not lower than the critical micelle concentration (CMC), a dilution process for preparing a dilute dispersion by diluting said pigment dispersion to a concentration below the critical micelle concentration (CMC), and a polymerization process for adding a monomer composition and a polymerization initiator to said dilute dispersion to achieve polymerization.

Also, it is preferably that the following formulas 1 and 2 be met, provided that the polymerization initiator concentration and monomer composition concentration in the polymerization process are written as A (mol/l) and B (mol/l), respectively:

$$0.001 \leq A \leq 0.03 \qquad \text{Formula I}$$

$$0.004 \leq (A/B) \leq 0.10 \qquad \text{Formula II}$$

The pigment-containing polymer particles of the present invention as containing an inorganic pigment are prepared by polymerization of a monomer composition containing at least one hydrophobic monomer in an aqueous dispersion of inorganic pigment particles dispersed in the presence of a surfactant, wherein the concentration of said surfactant at said polymerization is lower than the critical micelle concentration (CMC).

The inorganic pigment particles dispersed in the aqueous system are preferably coagulated particles having a particle size not greater than 20 times the primary particle size.

The pigment-containing polymer particles of the present invention as containing an inorganic pigment are prepared by polymerization of a monomer composition containing at least one hydrophobic monomer and 0.1 to 15% by weight of at least one hydrophilic monomer, wherein the concentration of said surfactant at said polymerization is lower than the critical micelle concentration (CMC).

The inorganic pigment particles dispersed in the aqueous system are preferably coagulated particles having a particle size not greater than 20 times the primary particle size.

The hydrophilic monomer as a component of the monomer composition is preferably at least one monomer selected from the group consisting of monomers containing the carboxyl group, monomers containing the sulfo group, primary amines, secondary amines, tertiary amines and quaternary ammonium salts, all capable of introducing a polar group to the side chain of the polymer.

The inorganic pigment particles are preferably at least one kind selected from the group consisting of carbon black, ferrite and magnetite.

The inorganic pigment particles have preferably been surface treated with a surface property improving agent.

The method of the present invention of producing pigment-containing polymer particles as containing an inorganic pigment comprises a pigment dispersion process for preparing a pigment dispersion by dispersing inorganic pigment particles in the presence of a surfactant at concentrations not lower than the critical micelle concentration (CMC), a dilution process for preparing a dilute dispersion by diluting said pigment dispersion to a concentration below the critical micelle concentration (CMC), and a polymerization process for adding a monomer composition and a polymerization initiator to said dilute dispersion to achieve polymerization.

It is preferable that the following formulas 1 and 2 be met, provided that the polymerization initiator concentration and monomer composition concentration in the polymerization process are written as A (mol/l) and B (mol/l), respectively:

$$0.002 \leq A \leq 0.02 \quad \text{Formula I}$$

$$0.005 \leq (A/B) \leq 0.10 \quad \text{Formula II}$$

The electrophotographic toner of the present invention are prepared by associating and fusing the foregoing pigment-containing polymer particles.

The immunological diagnostic reagent carrier of the present invention is prepared with the foregoing pigment-containing polymer particles.

DETAILED DESCRIPTION OF THE INVENTION

The present invention is hereinafter described in detail.

The pigment-containing polymer particles of the present invention are prepared by polymerization of a monomer composition in an aqueous dispersion of pigment particles dispersed in the presence of a surfactant.

Monomer Composition

The monomer composition for the pigment-containing polymer particles of the present invention contains a hydrophobic monomer as an essential component and contains a hydrophilic monomer and a crosslinkable monomer as necessary.

(1) Hydrophobic Monomer

The hydrophobic monomer as a component of the monomer composition may be any conventional monomer without limitation.

Specifically, radical polymerizable monomers such as monovinyl aromatic monomers, (meth)acrylate monomers, vinyl ester monomers, vinyl ether monomers, monoolefin monomers, diolefin monomers, halogenated olefin monomers and polyvinyl monomers can be preferably used.

Examples of monovinyl aromatic monomers include styrene monomers and derivatives thereof such as styrene, o-methylstyrene, m-methylstyrene, p-methylstyrene, p-methoxystyrene, p-phenylstyrene, p-chlorostyrene, p-ethylstyrene, p-n-butylstyrene, p-tert-butylstyrene, p-n-hexylstyrene, p-n-octylstyrene, p-n-nonylstyrene, p-n-decylstyrene, p-n-dodecylstyrene, 2,4-dimethylstyrene and 3,4-dichlorostyrene.

Examples of (meth)acrylate monomers include methyl acrylate, ethyl acrylate, butyl acrylate, acrylic acid-2-ethylhexyl, cyclohexyl acrylate, phenyl acrylate, methyl methacrylate, ethyl methacrylate, butyl methacrylate, hexyl methacrylate, methacrylic acid-2-ethylhexyl, ethyl $\beta$-hydroxyacrylate, propyl $\gamma$-aminoacrylate, stearyl methacrylate, dimethylaminoethyl methacrylate and diethylaminoethyl methacrylate.

Examples of vinyl ester monomers include vinyl acetate, vinyl propionate and vinyl benzoate.

Examples of vinyl ether monomers include vinyl methyl ether, vinyl ethyl ether, vinyl isobutyl ether and vinyl phenyl ether.

Examples of monoolefin monomers include ethylene, propylene, isobutylene, 1-butene, 1-pentene and 4-methyl-1-pentene.

Examples of diolefin monomers include butadiene, isoprene and chloroprene.

These hydrophobic monomers may be used singly or in combination.

(2) Hydrophilic Monomer

The hydrophilic monomer as a component of the monomer composition is not subject to limitation. For example, monomers containing the carboxyl group, monomers containing the sulfo group, monomers containing the primary amines, secondary amines, tertiary amines and quaternary ammonium salts, all capable of introducing a polar group to the side chain of the polymer, can be preferably used.

Examples of monomers containing the carboxyl group include acrylic acid, methacrylic acid, fumaric acid, maleic acid, iraconic acid, cinnamic acid, maleic acid monobutyl ester and maleic acid monooctyl ester.

Examples of monomers containing the sulfo group include styrenesulfonic acid and 2-acrylamidopropylsulfonic acid.

Examples of amine compounds include dimethylaminoethyl acrylate, dimethylaminoethyl methacrylate, diethylaminoethyl acrylate, diethylaminoethyl methacrylate, 3-dimethylaminophenyl acrylate and 2-hydroxy-3-methacryloxypropyltrimethylammonium salt.

These hydrophilic monomers may be used singly or in combination.

The incorporation of a hydrophilic monomer in the monomer composition results in 1) a greater rate of polymerization at polymerization, and 2) easier molecular weight control of the polymer. In addition, 3) as a result of polar group introduction to the polymer, chargeability can be controlled without charge control agents etc. when the particles are used as an electrophotographic toner.

The ratio of the hydrophilic monomer in the monomer composition is preferably 0.1 to 15% by weight, more preferably 0.5 to 12% by weight. If the ratio of the hydrophilic monomer is under 0.1% by weight, the above-described effect cannot be obtained sufficiently. If the ratio exceeds 15% by weight, the hydrophilic monomer alone undergoes polymerization, resulting in undesirable formation of a homopolymer.

(3) Crosslinkable Monomer

Examples of crosslinkable monomers include those with two or more unsaturated bonds, such as divinylbenzene, divinylnaphthalene, divinyl ether, diethylene glycol methacrylate, ethylene glycol dimethacrylate, polyethylene glycol dimethacrylate and diallyl phthalate.

The incorporation of a crosslinkable monomer in the monomer composition offers improved mechanical strength and other properties for the obtained pigment-containing polymer particles.

Pigment Particles

The pigment-containing polymer particles of the present invention are prepared by polymerization of a monomer composition in an aqueous dispersion of pigment particles (organic or inorganic pigment).

The pigment content in the pigment-containing polymer particles is 2 to 20 parts by weight, preferably 3 to 15 parts by weight per 100 parts by weight of the polymer components.

(1) Organic Pigment Particles

The organic pigment particles constituting the pigment-containing polymer particles may be particles of any conventional organic pigment without limitation.

Examples of useful organic pigments include magenta or red pigments such as C.I. Pigment Red 2, C.I. Pigment Red 3, C.I. Pigment Red 5, C.I. Pigment Red 6, C.I. Pigment Red 7, C.I. Pigment Red 15, C.I. Pigment Red 16, C.I. Pigment Red 48:1, C.I. Pigment Red 53:1, C.I. Pigment Red 57:1, C.I. Pigment Red 122, C.I. Pigment Red 123, C.I. Pigment Red 139, C.I. Pigment Red 139, C.I. Pigment Red 144, C.I. Pigment Red 149, C.I. Pigment Red 166, C.I. Pigment Red 177, C.I. Pigment Red 178 and C.I. Pigment Red 222, orange pigments such as C.I. Pigment Orange 31 and C.I. Pigment Orange 43, yellow pigments such as C.I. Pigment Yellow 12, C.I. Pigment Yellow 13, C.I. Pigment Yellow 14, C.I. Pigment Yellow 15, C.I. Pigment Yellow 17, C.I. Pigment Yellow 93, C.I. Pigment Yellow 94 and C.I. Pigment Yellow 138, cyan pigments such as C.I. Pigment Blue 15, C.I. Pigment Blue 15:2, C.I. Pigment Blue 15:3, C.I. Pigment Blue 16 and C.I. Pigment Blue 60, and green pigments such as C.I. Pigment Green 7. These pigments may be used singly or in combination.

(2) Inorganic Pigment Particles

The inorganic pigment particles constituting the pigment-containing polymer particles may also be particles of any conventional inorganic pigment without limitation.

Examples of preferable inorganic pigments include carbon black products such as furnace black, channel black, acetylene black, thermal black and lamp black, and magnetic powders such as ferrite and magnetite. These pigments may be used singly or in combination.

(3) Surface Treatment of Inorganic Pigment Particles

The inorganic pigment particles constituting the pigment-containing polymer particles have preferably been surface treated with a surface property improving agent.

Conventional surface property improving agents can be used for this purpose, with preference given to silane compounds, titanium compounds and aluminum compounds.

Examples of useful silane compounds include alkoxysilanes such as methyltrimethoxysilane, phenyltrimethoxysilane, methylphenyldimethoxysilane and diphenyldimethoxysilane, silazanes such as hexamethyldisilazane, $\gamma$-chloropropyltrimethoxysilane, vinyltrichlorosilane, vinyltrimethoxysilane, vinyltriethoxysilane, $\gamma$-methacryloxypropyltrimethoxysilane, $\gamma$-glycydoxypropyltrimethoxysilane, $\gamma$-mercaptopropyltrimethoxysilane, $\gamma$-aminopropyltriethoxysilane and $\gamma$-ureidopropyltriethoxysilane.

Examples of useful titanium compounds include TTS, 9S, 38S, 41B, 46B, 55, 138S and 238S (all produced by Ajinomoto Co., Inc.), A-1, B-1, TOT, TST, TAA, TAT, TLA, TOG, TBSTA, A-10, TBT, B-2, B-4, B-7, B-10, TBSTA-400, TTS, TOA-30, TSDMA, TTAB and TTOP (all produced by Nippon Soda Co., Ltd.).

Examples of useful aluminum compounds include AL-M (produced by Ajinomoto Co., Inc.).

The amount of these surface property improving agents used is 0.01 to 20% by weight, preferably 1 to 15% by weight of the inorganic pigment particles.

Surfactants

The pigment-containing polymer particles of the present invention are prepared by polymerization of an aqueous dispersion of pigment particles dispersed in the presence of a surfactant.

Examples of useful surfactants include sulfonates such as sodium dodecyl sulfonate, sodium dodecyl benzenesulfonate, sodium arylalkylpolyether sulfonate, sodium 3,3-disulfonediphenylurea-4,4-diazo-bis-amino-8-naphthol-6-sulfonate, ortho-carboxybenzene-azodimethylaniline and sodium 2,2,5,5-tetramethyltriphenylmethane-4,4-diazo-bis-$\beta$-naphthol-6-sulfonate, sulfates such as sodium tetradecylsulfate, sodium pentadecylsulfate and sodium octylsulfate, and fatty acid salts such as sodium oleate, sodium laurate, sodium caprate, sodium caprylate, sodium caproate, potassium stearate and calcium oleate.

Preparation of Pigment-containing Polymer Particles

The production method of the present invention is carried out while controlling the surfactant concentration in the aqueous system both at pigment dispersion and at polymerization.

Specifically, the pigment-containing polymer particles of the present invention can be efficiently produced by the following pigment dispersion process, dilution process and polymerization process.

(1) Pigment Dispersion Process

Pigment particles are dispersed in an aqueous system in the presence of a surfactant at concentrations of not lower than the critical micelle concentration (CMC) to yield a pigment dispersion.

This dispersion can be achieved by mechanical stirring using a sand grinder or the like, sonication using an ultrasound or the like, and compressive dispersion using High Pressure Homogenizer or the like.

Since pigment particles are difficult to disperse to primary particle levels, they are usually dispersed in the aqueous system in the form of coagulated primary particles.

The particle size of the pigment particles dispersed is preferably not greater than 10 times the primary particle size, more preferably not greater than 8 times, in the case of organic pigment particles. In the case of inorganic pigment particles, the particle size is preferably not greater than 20 times the primary particle size, more preferably not greater than 15 times the primary particle size.

If the pigment particles have too great a particle size, the desired pigment-containing polymer particles of small particle size cannot be produced, and pigment particles of great particle size migrate outside the reaction system, thus hampering pigment-polymer complexation.

In the pigment dispersion process, the surfactant concentration in the aqueous system need to be not lower than the critical micelle concentration (CMC).

Pigment particles of about 0.05 to 1 $\mu$m in particle size cannot be well dispersed, unless the surfactant concentration in the aqueous system is not lower than the critical micelle concentration (CMC).

(2) Dilution Process

The pigment dispersion prepared in the pigment dispersion process is diluted to a concentration below the critical micelle concentration (CMC) to yield a dilute dispersion.

(3) Polymerization Process

To the dilute dispersion prepared in the dilution process, a monomer composition and a polymerization initiator are added to cause polymerization.

Polymerization initiators preferably used to initiate the polymerization reaction include water-soluble radical polymerization initiators, including persulfates such as potassium persulfate and ammonium persulfate, azo compounds such as 4,4'-azobis-4-cyanovaleric acid, salts thereof and 2,2'-azobis(2-aminodipropane) salt, and peroxide compounds. Combinations of the above-mentioned polymerization initiators and reducing agents may be used as redox polymerization initiators of high polymerization activity. The use of a redox polymerization initiator allows the polymerization reaction to take place at low temperatures, offering polymerization time reduction.

With respect to the polymerization initiator concentration in the polymerization system, preferred ranges differ between organic pigment particles and inorganic pigment particles.

1) Organic Pigment Particles Used

When organic pigment particles are used, the polymerization initiator concentration is preferably 0.001 to 0.03 mol/l, more preferably 0.003 to 0.025 mol/l. Also, provided that the polymerization initiator concentration and monomer composition concentration are written as a (mol/l) and b (mol/l), respectively, the value a/b preferably falls within the range from 0.004 to 0.10. If the polymerization initiator concentration is too low, the polymerization reaction does not complete itself, leaving an unreacted monomer, due to a lack of radical production. If the polymerization initiator concentration is too high, soap-free polymerization occurs, resulting in the formation of a pigment-free polymer and hence phase separation between the polymer and the organic pigment, an undesirable aspect.

2) Inorganic Pigment Particles Used

When inorganic pigment particles are used, the polymerization initiator concentration is preferably 0.002 to 0.02 mol/l, more preferably 0.005 to 0.015 mol/l. Also, provided that the polymerization initiator concentration and monomer composition concentration are written as c (mol/l) and d (mol/l), respectively, the value c/d preferably falls within the range from 0.005 to 0.10. If the polymerization initiator concentration is too low, the polymerization reaction does not complete itself, leaving an unreacted monomer, due to a lack of radical production. If the polymerization initiator concentration is too high, soap-free polymerization occurs, resulting in the formation of a pigment-free polymer and hence phase separation between the polymer and the organic pigment, an undesirable aspect.

Although any temperature may be chosen for the polymerization reaction, as long as it is above the lowest radical formation temperature of the polymerization initiator, it is normally chosen between 50° C. and 80° C. The polymerization reaction may be carried out at normal temperatures using a combination of a normal temperature polymerization initiator such as hydrogen peroxide and a reducing agent such as ascorbic acid.

As stated above, the present invention is characterized in that an polymerization reaction is carried out under such conditions that the surfactant concentration is lower than the critical micelle concentration (CMC).

If the polymerization reaction is carried out under such conditions that the surfactant concentration is not lower than the critical micelle concentration (CMC), the monomer composition undergoes emulsification polymerization in the micelles in the aqueous system, resulting in the formation of pigment-free polymer particles. Applications of pigment-containing polymer particles With small particle size and excellent properties, the pigment-containing polymer particles of the present invention can be preferably used for such applications as electrophotographic toners, immunological diagnostic reagent carriers, liquid crystal display gap regulators, standard particles for particle size determination, chromatography column packings, cosmetic fillers and synthetic leather touch improving agents.

Electrophotographic toners and immunological diagnostic reagent carriers incorporating the pigment-containing polymer particles of the present invention are hereinafter described. 0059

(1) Electrophotographic Toners

Electrophotographic toner particles can be produced by associating and fusing the pigment-containing polymer particles of the present invention. The thus-obtained toner particles possess excellent properties for a component of an electrophotographic developing agent. It is particularly notable that their particle size distribution is sharp and they show little change over time and excellent durability.

The toner particles prepared from pigment-containing polymer particles may incorporate various internal and external additives.

Internal additives to toner particles include fixability improving agents such as low molecular polyethylene, low molecular polypropylene, acid-treated polyethylene, acid-treated polypropylene, acid-modified polyethylene and acid-modified polypropylene, positive charge control agents such as electron donor nigrosine dyes, metal salts of naphthenic acid, metal salts of higher fatty acid, alkoxylated amines, quaternary ammonium salts, alkylamides, metal complexes and fluorinating agents, and negative charge control agents such as organic electron acceptor complexes, chlorinated paraffins, chlorinated polyesters and sulfonylamines of copper phthalocyanine. These internal additives may be introduced to the toner particles by adding a required amount to the monomer composition.

External additives to toner particles include fluidizing agents consisting of fine powders of inorganic substances such as hydrophobic silica, titanium oxide, alumina, sulfides or nitrides thereof, and silicon carbide, charge control agents consisting of polyvinylidene fluoride powder, polystyrene powder, polymethyl methacrylate powder and fine polyethylene powder, and lubricants consisting of powders of metal salts of fatty acid.

(2) Immunological Diagnostic Reagent Carriers

The pigment-containing polymer particles of the present invention can be preferably used as an immunological diagnostic reagent carrier because their particle size is small and uniform and because their particle surface is free of foreign matter contamination.

When the pigment-containing polymer particles of the present invention are used as an immunological diagnostic reagent carrier, it is necessary to immobilize an immunologically active substance (e.g., antigen, antibody, receptor) on the surface thereof. This immobilization may be achieved by physical adsorption or chemical immobilization.

In the physical adsorption method, an immunologically active substance is physically adsorbed to, and immobilized on, the hydrophobic surface, offering immobilization without adsorption of immunologically active site [e.g., (Fab)'] using polymer particles obtained from, for example, styrene, derivatives thereof, (meth)acrylates or the like. When IgG is used as an antibody, (Fab')$_2$ or Fab', resulting from Fc fragment digestion, may be used.

In the chemical immobilization method, polymer particles are prepared by copolymerizing a monomer containing a functional group such as the carboxyl group, amino group or thiol group, and an immunologically active substance is reacted with the polymer particles and a known bifunctional reagent to immobilize the substance on the polymer particles. In the present invention, such a monomer containing a functional group may be used as a component of the monomer composition in producing pigment-containing polymer particles. The content ratio of the monomer containing a functional group in the monomer composition is preferably 0.1 to 15% by weight.

Although the antibody used may be polyclonal or monoclonal, it is preferred to use a polyclonal antibody when a coagulation test or coagulation inhibition test is conducted. When a monoclonal antibody is used, it is preferred to use several antibodies of different antigen binding sites in a mixture.

EXAMPLES

The present invention is hereinafter described in more detail by means of the following examples, which are not to be construed as limitative.

The particle size of the pigment particles dispersed in the pigment dispersion and the particle size of the obtained pigment-containing polymer particles were determined using an electrophoretic light scattering photometer ELS-800 (produced by OTSUKA ELECTRONICS CO., LTD.).

Example 1-A (1) Preparation of Pigment Dispersion

After 6.5 g of C.I. Pigment Blue 15:3 (organic pigment, primary particle size 80 nm), 1.38 g of sodium dodecyl sulfate (surfactant, CMC $=8.1\times10^{-33}$ mol/l) and 200 ml of degassed deionized water were mixed together, the organic pigment was dispersed using a compressire mechanical disperser, to yield a pigment dispersion (surfactant concentration$=2.4\times10^{-32}$ mol/l).

The organic pigment particles dispersed in the pigment dispersion had an average particle size $d_{50}$ of 0.23 μm and a CV value of 0.17.

(2) Preparation of Pigment-containing Polymer Particles

To a 500 ml cylindrical separable flask equipped with a temperature sensor, a nitrogen blowing tube and a mechanical stirrer (with a disc turbine type impeller blades), 50 ml of the pigment dispersion prepared in term (1) above, 250 ml of degassed deionized water and 31.2 g of styrene (hydrophobic monomer, 0.3 mol) were placed (surfactant concentration$=4\times10^{-33}$ mol/l), and the contents of the flask was heated in a nitrogen atmosphere while stirring at a rate of 300 rpm.

When the reaction system temperature reached 70° C., 0.87 g of the polymerization initiator potassium persulfate (polymerization initiator concentration 0.01 mol/l) was added to initiate polymerization. After 7 hours of the polymerization reaction, the pigment-containing polymer particles of the present invention were obtained.

Transmission electron microscopy (TEM) of the obtained pigment-containing polymer particles revealed complexation of the organic pigment and the polymer.

The pigment-containing polymer particles had an average particle size $d_{50}$ of 0.26 μm and a CV value of 0.19, demonstrating small particle size and excellent monodispersibility.

Example 1-B

A pigment dispersion was prepared in the same manner as in Example 1-A, except that C.I. Pigment Blue 15:3 was replaced with C.I. Pigment Red 122 (organic pigment, primary particle size 95 nm). The organic pigment particles dispersed in the pigment dispersion had an average particle size $d_{50}$ of 0.32 μm and a CV value of 0.22.

Next, the same procedure as in Example 1-A was followed, except that this pigment dispersion was used, to yield the pigment-containing polymer particles of the present invention. Transmission electron microscopy (TEM) of the obtained pigment-containing polymer particles revealed complexation of the organic pigment and the polymer. The pigment-containing polymer particles had an average particle size $d_{50}$ of 0.34 μm and a CV value of 0.24, demonstrating small particle size and excellent monodispersibility.

Example 1-C

A pigment dispersion was prepared in the same manner as in Example 1-A, except that C.I. Pigment Blue 15:3 was replaced with C.I. Pigment Yellow 17 (organic pigment, primary particle size 100 nm). The organic pigment particles dispersed in the pigment dispersion had an average particle size $d_{50}$ of 0.49 μm and a CV value of 0.28.

Next, the same procedure as in Example 1-A was followed, except that this pigment dispersion was used, to yield the pigment-containing polymer particles of the present invention. Transmission electron microscopy (TEM) of the obtained pigment-containing polymer particles revealed complexation of the organic pigment and the polymer. The pigment-containing polymer particles had an average particle size $d_{50}$ of 0.50 μm and a CV value of 0.30, demonstrating small particle size and excellent monodispersibility.

Example 1-D

A pigment dispersion was prepared in the same manner as in Example 1-A, except that the amount of sodium dodecyl sulfate used at pigment dispersion was 0.52 g (surfactant concentration = $9.0 \times 10^{-33}$ mol/l). The organic pigment particles dispersed in the pigment dispersion medium had an average particle size $d_{50}$ of 0.28 μm and a CV value of 0.19.

Next, the same procedure as in Example 1-A, the polymerization reaction was followed (surfactant concentration = $1.5 \times 10^{-33}$ mol/l), except that this pigment dispersion was used, to yield the pigment-containing polymer particles of the present invention. Transmission electron microscopy (TEM) of the obtained pigment-containing polymer particles revealed complexation of the organic pigment and the polymer. The pigment-containing polymer particles had an average particle size $d_{50}$ of 0.30 μm and CV value of 0.21, demonstrating small particle size and excellent monodispersibility.

Example 1-E

A pigment dispersion was prepared in the same manner as in Example 1-A, except that the amount of sodium dodecyl sulfate used at pigment dispersion was 2.42 g (surfactant concentration = $4.2 \times 10^{-32}$ mol/l). The organic pigment particles dispersed in the pigment dispersion medium had an average particle size $d_{50}$ of 0.21 μm and a CV value of 0.16.

Next, the same procedure as in Example 1-A, the polymerization reaction was followed (surfactant concentration = $7.0 \times 10^{-33}$ mol/l), except that this pigment dispersion was used, to yield the pigment-containing polymer particles of the present invention. Transmission electron microscopy (TEM) of the obtained pigment-containing polymer particles revealed complexation of the organic pigment and the polymer. The pigment-containing polymer particles had an average particle size $d_{50}$ of 0.23 μm and CV value of 0.18, demonstrating small particle size and excellent monodispersibility.

Comparative Example 1-a

A pigment dispersion was prepared in the same manner as in Example 1-A, except that the amount of sodium dodecyl sulfate used at pigment dispersion was 0.40 g (surfactant concentration = $7.0 \times 10^{-33}$ mol/l). The organic pigment particles dispersed in the pigment dispersion medium had an average particle size $d_{50}$ of 0.84 μm and a CV value of 0.63. The particle distribution was very wide.

Next, the same procedure as in Example 1-A, the polymerization reaction was followed (surfactant concentration = $1.5 \times 10^{-33}$ mol/l), except that this pigment dispersion was used, to yield the pigment-containing polymer particles. The obtained pigment-containing polymer particles had an average particle size $d_{50}$ of 1.53 μm and CV value of 0.92. Due to the wide distribution of the particle size, a part of polymers were coagulated to form agglomerates and the pigment-containing polymer particles of small particle size and excellent monodispersibility were not obtained.

Comparative Sample 1-b

An attempt was made to prepare pigment-containing polymer particles in the same manner as in Example 1-A, except that the amount of sodium dodecyl sulfate used at pigment dispersion was 3.50 g (surfactant concentration = $6.1 \times 10^{-2}$ mol/l at pigment dispersion, $1.0 \times 10^{-2}$ mol/l at polymerization reaction), but complexation of the polymer and the organic pigment particles failed due to phase separation.

For the foregoing examples and comparative examples, the conditions of preparation of (pigment-containing) polymer particles, and the average particle sizes and CV values of the pigment-containing polymer particles are given in Table 1.

TABLE 1

| | | Pigment dispersion | | Polymerization reaction system | | | Pigment-containing polymer particles | |
|---|---|---|---|---|---|---|---|---|
| | | Pigment particle size | | Surfactant concentration (before dilution) (mol/l) | Surfactant concentration (after dilution) (mol/l) | Polymerization initiator concentration (mol/l) | Polymerization initiator/ monomer composition | |
| | C.I. Pigment | Average particle size (μm) | CV value | | | | | Average particle size (μm) | CV value |
| Example 1-A | Blue 15:3 | 0.23 | 0.17 | $2.4 \times 10^{-2}$ | $4.0 \times 10^{-3}$ | 0.01 | 0.01 | 0.26 | 0.19 |
| Example 1-B | Red 122 | 0.32 | 0.22 | $2.4 \times 10^{-2}$ | $4.0 \times 10^{-3}$ | 0.01 | 0.01 | 0.34 | 0.24 |
| Example 1-C | Yellow 17 | 0.49 | 0.28 | $2.4 \times 10^{-2}$ | $4.0 \times 10^{-3}$ | 0.01 | 0.01 | 0.50 | 0.30 |
| Example 1-D | Blue 15:3 | 0.28 | 0.19 | $9.0 \times 10^{-3}$ | $1.5 \times 10^{-3}$ | 0.01 | 0.01 | 0.30 | 0.21 |
| Example 1-E | Blue 15:3 | 0.21 | 0.16 | $4.2 \times 10^{-2}$ | $7.0 \times 10^{-3}$ | 0.01 | 0.01 | 0.23 | 0.18 |
| Comparative Example 1-a | Blue 15:3 | 0.84 | 0.63 | $7.0 \times 10^{-3}$ | $1.2 \times 10^{-3}$ | 0.01 | 0.01 | 1.53 | 0.92 |
| Comparative Example 1-b | Blue 15:3 | 0.23 | 0.17 | $6.1 \times 10^{-2}$ | $1.0 \times 10^{-2}$ | 0.01 | 0.01 | Complexation failed | |

Example 2-A

The pigment-containing polymer particles of the present invention were prepared in the same manner as in Example 1-A, except that 29.6 g of styrene (hydrophobic monomer, 0.28 mol) and 1.6 g of a methacrylic acid monomer (hydrophilic monomer, 0.02 mol) were used as components of the monomer composition.

Transmission electron microscopy (TEM) of the obtained pigment-containing polymer particles revealed complexation of the organic pigment and the polymer.

The pigment-containing polymer particles had an average particle size $d_{50}$ of 0.28 μm and a CV value of 0.20, demonstrating small particle size and excellent monodispersibility.

Example 2-B

A pigment dispersion was prepared in the same manner as in Example 2-A, except that C.I. Pigment Blue 15:3 was replaced with C.I. Pigment Red 12 (organic pigment, primary particle size 95 nm). Next, the same procedure as in Example 2-A was followed, except that this pigment dispersion was used, to yield the pigment-containing polymer particles of the present invention. Transmission electron microscopy (TEM) of the obtained pigment-containing polymer particles revealed complexation of the organic pigment and the polymer. The pigment-containing polymer particles had an average particle size $d_{50}$ of 0.37 μm and a CV value of 0.26, demonstrating small particle size and excellent monodispersibility.

Example 2-C

A pigment dispersion was prepared in the same manner as in Example 2-A, except that C.I. Pigment Blue 15:3 was replaced with C.I. Pigment Yellow 17 (organic pigment, primary particle size 100 nm). Next, the same procedure as in Example 2-A was followed, except that this pigment dispersion was used, to yield the pigment-containing polymer particles of the present invention. Transmission electron microscopy (TEM) of the obtained pigment-containing polymer particles revealed complexation of the organic pigment and the polymer. The pigment-containing polymer particles had an average particle size $d_{50}$ of 0.54 μm and a CV value of 0.34, demonstrating small particle size and excellent monodispersibility.

Example 2-D

A pigment dispersion was prepared in the same manner as in Example 2-A, except that the amount of sodium dodecyl sulfate used at pigment dispersion was 0.52 g (surfactant concentration=$9.0 \times 10^{-3}$ mol/l). The organic pigment particles dispersed in the pigment dispersion medium had an average particle size $d_{50}$ of 0.28 μm and a CV value of 0.19.

Next, the same procedure as in Example 2-A, the polymerization reaction was followed (surfactant concentration=$1.5 \times 10^{-3}$ mol/l), except that this pigment dispersion was used, to yield the pigment-containing polymer particles of the present invention. Transmission electron microscopy (TEM) of the obtained pigment-containing polymer particles revealed complexation of the organic pigment and the polymer. The pigment-containing polymer particles had an average particle size $d_{50}$ of 0.33 μm and CV value of 0.24, demonstrating small particle size and excellent monodispersibility.

Example 2-E

A pigment dispersion was prepared in the same manner as in Example 2-A, except that the amount of sodium dodecyl sulfate used at pigment dispersion was 2.42 g (surfactant concentration=$4.2 \times 10^{-2}$ mol/l). The organic pigment particles dispersed in the pigment dispersion medium had an average particle size $d_{50}$ of 0.21 μm and a CV value of 0.16.

Next, the same procedure as in Example 2-A, the polymerization reaction was followed (surfactant concentration=$7.0 \times 10^{-3}$ mol/l), except that this pigment dispersion was used, to yield the pigment-containing polymer particles of the present invention. Transmission electron microscopy (TEM) of the obtained pigment-containing polymer particles revealed complexation of the organic pigment and the polymer. The pigment-containing polymer particles had an average particle size $d_{50}$ of 0.25 μm and CV value of 0.21, demonstrating small particle size and excellent monodispersibility.

Comparative Example 2-a

A pigment dispersion was prepared in the same manner as in Example 2-A, except that the amount of sodium dodecyl sulfate used at pigment dispersion was 0.40 g (surfactant concentration=$7.0 \times 10^{-3}$ mol/l). The organic pigment particles dispersed in the pigment dispersion medium had an average particle size $d_{50}$ of 0.84 μm and a CV value of 0.63. The particle distribution was very wide.

Next, the same procedure as in Example 1-A, the polymerization reaction was followed (surfactant concentration=$1.2 \times 10^{-3}$ mol/l), except that this pigment dispersion was used, to yield the pigment-containing polymer particles. The obtained pigment-containing polymer particles had an average particle size $d_{50}$ of 1.82 μm and Cv value of 0.86. Due to the wide distribution of the particle size, a part of polymers were coagulated to form agglomerates and the pigment-containing polymer particles of Small particle size and excellent monodispersibility were not obtained.

Comparative Sample 2-b

An attempt was made to prepare pigment-containing polymer particles in the same manner as in Example 2-A, except that the amount of sodium dodecyl sulfate used at pigment dispersion was 3.50 g (surfactant concentration=$6.1 \times 10^{-2}$ mol/l at pigment dispersion, $1.0 \times 10^{-2}$ mol/l at polymerization reaction), but complexation of the polymer and the organic pigment particles failed due to phase separation.

For the foregoing examples and comparative examples, the conditions of preparation of (pigment-containing) polymer particles, and the average particle sizes and CV values of the pigment-containing polymer particles are given in Table 2.

TABLE 2

| | | Pigment dispersion | | | Polymerization reaction system | | | Pigment-containing polymer particles | |
|---|---|---|---|---|---|---|---|---|---|
| | | Pigment particle size | | Surfactant concentration (before dilution) (mol/l) | Surfactant concentration (after dilution) (mol/l) | Polymerization initiator concentration (mol/l) | Polymerization initiator/monomer composition | | |
| | C.I. Pigment | Average particle size (μm) | CV value | | | | | Average particle size (μm) | CV value |
| Example 2-A | Blue 15:3 | 0.23 | 0.17 | $2.4 \times 10^{-2}$ | $4.0 \times 10^{-3}$ | 0.01 | 0.01 | 0.28 | 1.20 |
| Example 2-B | Red 122 | 0.32 | 0.22 | $2.4 \times 10^{-2}$ | $4.0 \times 10^{-3}$ | 0.01 | 0.01 | 0.37 | 0.26 |
| Example 2-C | Yellow 17 | 0.49 | 0.28 | $2.4 \times 10^{-2}$ | $4.0 \times 10^{-3}$ | 0.01 | 0.01 | 0.54 | 0.34 |
| Example 2-D | Blue 15:3 | 0.28 | 0.19 | $9.0 \times 10^{-3}$ | $1.5 \times 10^{-3}$ | 0.01 | 0.01 | 0.33 | 0.24 |
| Example 2-E | Blue 15:3 | 0.21 | 0.16 | $4.2 \times 10^{-2}$ | $7.0 \times 10^{-3}$ | 0.01 | 0.01 | 0.25 | 0.21 |
| Comparative Example 2-a | Blue 15:3 | 0.84 | 0.63 | $7.0 \times 10^{-3}$ | $1.2 \times 10^{-3}$ | 0.01 | 0.01 | 1.82 | 0.86 |
| Comparative Example 2-b | Blue 15:3 | 0.23 | 0.17 | $6.1 \times 10^{-2}$ | $1.0 \times 10^{-2}$ | 0.01 | 0.01 | Complexation failed | |

Example 3-A (1) Surface Treatment of Inorganic Pigment Particles

To a 500 ml cylindrical separable flask, 200 ml of n-hexane and 20 g of carbon black were added, and 0.4 g of AL-M (surface treating agent) was added. While stirring at a rate of 200 rpm, the contents of the flask was heated to 68° C.; the carbon black was surface treated while maintaining this state for 2 hours. The surface treated carbon black was filtered and then dried at 120° C. under reduced pressure.

(2) Preparation of Pigment Dispersion

After 6.5 g of the carbon black thus surface treated (inorganic pigment, primary particle size 25 nm), 1.38 g of sodium dodecyl sulfate (surfactant, CMC=$8.1 \times 10^{-3}$ mol/l) and 200 ml of degassed deionized water were mixed together, the inorganic pigment was dispersed using a compressive mechanical disperser to yield a pigment dispersion (surfactant concentration=$2.4 \times 10^{-2}$ mol/l).

The inorganic pigment particles dispersed in the pigment dispersion had an average particle size $d_{50}$ of 0.12 μm and a CV value of 0.13.

(3) Production of Pigment-containing Polymer Particles

To a 500 ml cylindrical separable flask equipped with a temperature sensor, a nitrogen blowing tube and a mechanical stirrer (with a disc turbine type impeller blades), 50 ml of the pigment dispersion prepared in term (1) above, 250 ml of degassed deionized water and 31.2 g of styrene (hydrophobic monomer, 0.3 mol) were placed (surfactant concentration=$4 \times 10^{-3}$ mol/l), and the contents of the flask was heated in a nitrogen atmosphere while stirring at a rate of 300 rpm.

When the reaction system temperature reached 70° C., 0.87 g of the polymerization initiator potassium persulfate (polymerization initiator concentration 0.01 mol/l) was added to initiate polymerization. After 7 hours of the polymerization reaction, the pigment-containing polymer particles of the present invention were obtained.

Transmission electron microscopy (TEM) of the obtained pigment-containing polymer particles revealed complexation of the inorganic pigment and the polymer.

The pigment-containing polymer particles had an average particle size $d_{50}$ of 0.15 μm and a CV value of 0.16, demonstrating small particle size and excellent monodispersibility.

Example 3-B

A pigment dispersion was prepared in the same manner as in Example 3-A, except that carbon black was replaced with magnetite (inorganic pigment, primary particle size 45 nm). The inorganic pigment particles dispersed in the pigment dispersion had an average particle size $d_{50}$ of 0.35 μm and a CV value of 0.17.

Next, the same procedure as in Example 3-A was followed, except that this pigment dispersion was used, to yield the pigment-containing polymer particles of the present invention. Transmission electron microscopy (TEM) of the obtained pigment-containing polymer particles revealed complexation of the inorganic pigment and the polymer. The pigment-containing polymer particles had an average particle size $d_{50}$ of 0.38 μm and a CV value of 0.19, demonstrating small particle size and excellent monodispersibility.

Example 3-C

A pigment dispersion was prepared in the same manner as in Example 3-A, except that carbon black was replaced with ferrite (inorganic pigment, primary particle size 50 nm). The inorganic pigment particles dispersed in the pigment dispersion had an average particle size $d_{50}$ of 0.42 μm and a CV value of 0.22.

Next, the same procedure as in Example 3-A was followed, except that this pigment dispersion was used, to yield the pigment-containing polymer particles of the present invention. Transmission electron microscopy (TEM) of the obtained pigment-containing polymer particles revealed complexation of the inorganic pigment and the polymer. The pigment-containing polymer particles had an average particle size $d_{50}$ of 0.43 μm and a CV value of 0.24, demonstrating small particle size and excellent monodispersibility.

Example 3-D

A pigment dispersion was prepared in the same manner as in Example 3-A, except that the amount of sodium dodecyl sulfate used at pigment dispersion was 0.52 g (surfactant concentration=$9.0 \times 10^{-3}$ mol/l). The inorganic pigment particles dispersed in the pigment dispersion medium had an average particle size $d_{50}$ of 0.17 μm and a CV value of 0.14.

Next, the same procedure as in Example 3-A, the polymerization reaction was followed (surfactant concentration=$1.5 \times 10^{-3}$ mol/l), except that this pigment dispersion was used, to yield the pigment-containing polymer particles of the present invention. Transmission electron microscopy (TEM) of the obtained pigment-containing polymer particles revealed complexation of the inorganic pigment and the polymer. The pigment-containing polymer particles had an average particle size $d_{50}$ of 0.20 μm and CV value of 0.15, demonstrating small particle size and excellent monodispersibility.

Example 3-E

A pigment dispersion was prepared in the same manner as in Example 3-A, except that the amount of sodium dodecyl sulfate used at pigment dispersion was 2.42 g (surfactant concentration=$4.2\times10^{-2}$ mol/l). The inorganic pigment particles dispersed in the pigment dispersion medium had an average particle size $d_{50}$ of 0.11 μm and a CV value of 0.13.

Next, the same procedure as in Example 3-A, the polymerization reaction was followed (surfactant concentration=$7.0\times10^{-3}$ mol/l), except that this pigment dispersion was used, to yield the pigment-containing polymer particles of the present invention. Transmission electron microscopy (TEM) of the obtained pigment-containing polymer particles revealed complexation of the inorganic pigment and the polymer. The pigment-containing polymer particles had an average particle size $d_{50}$ of 0.14 μm and CV value of 0.15, demonstrating small particle size and excellent monodispersibility.

Comparative Example 3-a

A pigment dispersion was prepared in the same manner as in Example 3-A, except that the amount of sodium dodecyl sulfate used at pigment dispersion was 0.40 g (surfactant concentration=$7.0\times10^{-3}$ mol/l). The inorganic pigment particles dispersed in the pigment dispersion medium had an average particle size $d_{50}$ of 0.36 μm and a CV value of 0.58. The particle distribution was very wide.

Next, the same procedure as in Example 3-A, the polymerization reaction was followed (surfactant concentration=$1.2\times10^{-3}$ mol/l), except that this pigment dispersion was used, to yield the pigment-containing polymer particles. The obtained pigment-containing polymer particles had an average particle size $d_{50}$ of 1.37 μm and CV value of 0.87. Due to the wide distribution of the particle size, a part of polymers were coagulated to form agglomerates and the pigment-containing polymer particles of small particle size and excellent monodispersibility were not obtained.

Comparative Sample 3-b

An attempt was made to prepare pigment-containing polymer particles in the same manner as in Example 3-A, except that the amount of sodium dodecyl sulfate used at pigment dispersion was 3.50 g (surfactant concentration=$6.1\times10^{-2}$ mol/l at pigment dispersion, $1.0\times10^{-2}$ mol/l at polymerization reaction), but complexation of the polymer and the inorganic pigment particles failed due to phase separation.

For the foregoing examples and comparative examples, the conditions of preparation of (pigment-containing) polymer particles, and the average particle sizes and CV values of the pigment-containing polymer particles are given in Table 3.

TABLE 3

| | | Pigment dispersion | | Polymerization reaction system | | | Pigment-containing polymer particles | |
|---|---|---|---|---|---|---|---|---|
| | | Pigment particle size | | Surfactant concentration (before dilution) (mol/l) | Surfactant concentration (after dilution) (mol/l) | Polymerization initiator concentration (mol/l) | | |
| | Pigment particle material | Average particle size (μm) | CV value | | | | Polymerization initiator/monomer composition | Average particle size (μm) | CV value |
| Example 3-A | Carbon black | 0.12 | 0.13 | $2.4\times10^{-2}$ | $4.0\times10^{-3}$ | 0.01 | 0.01 | 0.15 | 0.16 |
| Example 3-B | Magnetite | 0.35 | 0.17 | $2.4\times10^{-2}$ | $4.0\times10^{-3}$ | 0.01 | 0.01 | 0.38 | 0.19 |
| Example 3-C | Ferrite | 0.42 | 0.22 | $2.4\times10^{-2}$ | $4.0\times10^{-3}$ | 0.01 | 0.01 | 0.43 | 0.24 |
| Example 3-D | Carbon black | 0.17 | 0.14 | $9.0\times10^{-3}$ | $1.5\times10^{-3}$ | 0.01 | 0.01 | 0.20 | 0.15 |
| Example 3-E | Carbon black | 0.11 | 0.13 | $4.2\times10^{-2}$ | $7.0\times10^{-3}$ | 0.01 | 0.01 | 0.14 | 0.15 |
| Comparative Example 3-a | Carbon black | 0.36 | 0.58 | $7.0\times10^{-3}$ | $1.2\times10^{-3}$ | 0.01 | 0.01 | 1.37 | 0.87 |
| Comparative Example 3-b | Carbon black | 0.12 | 0.13 | $6.1\times10^{-2}$ | $1.0\times10^{-2}$ | 0.01 | 0.01 | Complexation failed | |

Example 4-A

The pigment-containing polymer particles of the present invention were prepared in the same manner as in Example 3-A, except that 29.6 g of styrene (hydrophobic monomer, 0.28 mol) and 1.6 g of a methacrylic acid monomer (hydrophilic monomer, 0.02 mol) were used as components of the monomer composition.

Transmission electron microscopy (TEM) of the obtained pigment-containing polymer particles revealed complexation of the inorganic pigment and the polymer.

The pigment-containing polymer particles had an average particle size $d_{50}$ of 0.17 μm and a Cv value of 0.17, demonstrating small particle size and excellent monodispersibility.

Example 4-B

A pigment dispersion was prepared in the same manner as in Example 4-A, except that carbon black was replaced with magnetite (inorganic pigment, primary particle size 45 nm). Next, the same procedure as in Example 4-A was followed, except that this pigment dispersion was used, to yield the pigment-containing polymer particles of the present invention. Transmission electron microscopy (TEM) of the obtained pigment-containing polymer particles revealed complexation of the inorganic pigment and the polymer. The pigment-containing polymer particles had an average particle size $d_{50}$ of 0.41 μm and a CV value of 0.21, demonstrating small particle size and excellent monodispersibility.

Example 4-C

A pigment dispersion was prepared in the same manner as in Example 4-A, except that carbon black was replaced with ferrite (inorganic pigment, primary particle size 50 nm). Next, the same procedure as in Example 4-A was followed, except that this pigment dispersion was used, to yield the pigment-containing polymer particles of the present invention. Transmission electron microscopy (TEM) of the obtained pigment-containing polymer particles revealed complexation of the inorganic pigment and the polymer. The pigment-containing polymer particles had an average particle size $d_{50}$ of 0.48 μm and a CV value of 0.25, demonstrating small particle size and excellent monodispersibility.

Example 4-D

A pigment dispersion was prepared in the same manner as in Example 4-A, except that the amount of sodium dodecyl sulfate used at pigment dispersion was 0.52 g (surfactant concentration $= 9.0 \times 10^{-3}$ mol/l). The inorganic pigment particles dispersed in the pigment dispersion medium had an average particle size $d_{50}$ of 0.17 μm and a CV value of 0.14.

Next, the same procedure as in Example 4-A, the polymerization reaction was followed (surfactant concentration $= 1.5 \times 10^{-3}$ mol/l), except that this pigment dispersion was used, to yield the pigment-containing polymer particles of the present invention. Transmission electron microscopy (TEM) of the obtained pigment-containing polymer particles revealed complexation of the inorganic pigment and the polymer. The pigment-containing polymer particles had an average particle size $d_{50}$ of 0.23 μm and CV value of 0.16, demonstrating small particle size and excellent monodispersibility.

Example 4-E

A pigment dispersion was prepared in the same manner as in Example 4-A, except that the amount of sodium dodecyl sulfate used at pigment dispersion was 2.42 g (surfactant concentration $= 4.2 \times 10^{-2}$ mol/l). The inorganic pigment particles dispersed in the pigment dispersion medium had an average particle size $d_{50}$ of 0.11 μm and a CV value of 0.13.

Next, the same procedure as in Example 4-A, the polymerization reaction was followed (surfactant concentration $= 7.0 \times 10^{-3}$ mol/l), except that this pigment dispersion was used, to yield the pigment-containing polymer particles of the present invention. Transmission electron microscopy (TEM) of the obtained pigment-containing polymer particles revealed complexation of the inorganic pigment and the polymer. The pigment-containing polymer particles had an average particle size $d_{50}$ of 0.16 μm and CV value of 0.15, demonstrating small particle size and excellent monodispersibility.

Comparative Example 4-a

A pigment dispersion was prepared in the same manner as in Example 4-A, except that the amount of sodium dodecyl sulfate used at pigment dispersion was 0.40 g (surfactant concentration $= 7.0 \times 10^{-3}$ mol/l). The inorganic pigment particles dispersed in the pigment dispersion medium had an average particle size $d_{50}$ of 0.36 μm and a CV value of 0.58. The particle distribution was very wide.

Next, the same procedure as in Example 4-A, the polymerization reaction was followed (surfactant concentration $= 1.2 \times 10^{-3}$ mol/l), except that this pigment dispersion was used, to yield the pigment-containing polymer particles. The obtained pigment-containing polymer particles had an average particle size $d_{50}$ of 1.54 μm and CV value of 0.93. Due to the wide distribution of the particle size, a part of polymers were coagulated to form agglomerates and the pigment-containing polymer particles of small particle size and excellent monodispersibility were not obtained.

Comparative Sample 4-b

An attempt was made to prepare pigment-containing polymer particles in the same manner as in Example 4-A, except that the amount of sodium dodecyl sulfate used at pigment dispersion was 3.50 g (surfactant concentration $= 6.1 \times 10^{-2}$ mol/l at pigment dispersion, $1.0 \times 10^{-2}$ mol/l at polymerization reaction), but complexation of the polymer and the organic pigment particles failed due to phase separation.

For the foregoing examples and comparative examples, the conditions of preparation of (pigment-containing) polymer particles, and the average particle sizes and CV values of the pigment-containing polymer particles are given in Table 4.

TABLE 4

| | | Pigment dispersion | | | Polymerization reaction system | | | Pigment-containing polymer particles | |
|---|---|---|---|---|---|---|---|---|---|
| | | Pigment particle size | | Surfactant concentration | Surfactant concentration | Polymerization initiator concentration | Polymerization initiator/ monomer composition | | |
| | Pigment particle material | Average particle size (μm) | CV value | (before dilution) (mol/l) | (after dilution) (mol/l) | (mol/l) | | Average particle size (μm) | CV value |
| Example 4-A | Carbon black | 0.12 | 0.13 | $2.4 \times 10^{-2}$ | $4.0 \times 10^{-3}$ | 0.01 | 0.01 | 0.17 | 0.17 |
| Example 4-B | Magnetite | 0.35 | 0.17 | $2.4 \times 10^{-2}$ | $4.0 \times 10^{-3}$ | 0.01 | 0.01 | 0.41 | 0.21 |
| Example 4-C | Ferrite | 0.42 | 0.22 | $2.4 \times 10^{-2}$ | $4.0 \times 10^{-3}$ | 0.01 | 0.01 | 0.48 | 0.25 |
| Example 4-D | Carbon black | 0.17 | 0.14 | $9.0 \times 10^{-3}$ | $1.5 \times 10^{-3}$ | 0.01 | 0.01 | 0.23 | 0.16 |
| Example 4-E | Carbon black | 0.11 | 0.13 | $4.2 \times 10^{-2}$ | $7.0 \times 10^{-3}$ | 0.01 | 0.01 | 0.16 | 0.15 |
| Comparative Example 4-a | Carbon black | 0.36 | 0.58 | $7.0 \times 10^{-3}$ | $1.2 \times 10^{-3}$ | 0.01 | 0.01 | 1.54 | 0.93 |
| Comparative Example 4-b | Carbon black | 0.12 | 0.13 | $6.1 \times 10^{-2}$ | $1.0 \times 10^{-2}$ | 0.01 | 0.01 | Complexation failed | |

Evaluation of Electrophotographic Toner

Evaluation Example I-1

(1) Preparation of Toners

Pigment-containing polymer particles obtained in Examples 1-A, 1-B and 1-C, respectively, were coagulated in accordance with the method described in Japanese Patent Publication Open to Public Inspection No. 259156/1991, and then dried and disintegrated to yield toner particles of 5 μm in average particle size.

To each toner obtained (hereinafter referred to as toner 1A, toner 1B and toner 1C, respectively), fine silica grains R-972 (produced by NIHON AEROGIL CO., LTD.) were added at 20% by weight, and fine titanium oxide grains T-805 (produced by NIHON AEROGIL CO., LTD.) were added at 1.0% by weight.

(2) Preparation of Carrier

A resin-coated carrier was prepared wherein a resin-coating layer of a methyl methacrylate-styrene copolymer has been formed on the surface of the core particles.

(3) Preparation of Developing Agents

Each of toners 1A through 1C and the above-described resin-coated carrier were mixed to a toner concentration of 5% by weight, to yield developing agents 1A through 1C.

(4) Actual Picture Taking Test

Each of the thus-obtained developing agents 1A through 1C was subjected to an actual picture taking test under normal temperature/humidity conditions (20° C., 60% RH) using an electrophotographic copying machine U-Bix 3032 (produced by Konica Corporation) equipped with a heat roller fixer and a cleaning blade. Changes over time in 1) resolution, 2) fogging, 3) offset resistance, 4) toner coloring, 5) cleanability and 6) toner particle size distribution were evaluated.

These items were evaluated as follows:

1) Resolution

A copy of a thin line chart was taken, and the number of recognizable lines per mm was counted.

2) Fogging

A series of continuously taken copies were assessed as to the reflection density of each color on the white background, using Sakura Densitometer PDA-60 (produced by Konica Corporation). The number of copies at the time of fogging was counted, in which fogging density was set at 0.02.

3) Offset Resistance (Offset Temperature)

Copy images were taken at step by step changed fixing roller temperature setting, and the fixing roller temperature setting was obtained at the time of toner stain due to hot offset. This temperature was taken as the offset temperature.

4) Toner Coloring (Toner Reflection Density)

Each toner was attached in a single layer to a white label, and the toner layer was assessed as to the reflection density of each color, using Sakura Densitometer PDA-60 (produced by Konica Corporation). When the reflection density was not lower than 1.3, rating "A" was given; when the reflection density was lower than 1.3, rating "B" was given.

5) Cleanability

The surface of each photoreceptor was macroscopically observed. The number of copies at the occurrence of cleaning failure was counted.

6) Changes over Time in Particle Size Distribution

The ratio by number (number %) of toner particles whose particle size was not greater than one-third of the volume-average particle size was determined at the initial stage (start of the actual picture taking test), at fogging or at 50000 copies had been taken. If the number ratio exceeds 10%, toner chargeability tends to be affected. Toner particle size was determined using a laser diffraction particle size meter SALD-1100 (produced by Shimadzu Corporation).

The results are given in Table 5 below.

Evaluation Example I-2

Toner particles of 5 μm in average particle size were prepared in the same manner as in Evaluation Example I-1, except that the pigment-containing polymer particles obtained in Examples 2-A, 2-B and 2-C, respectively, were used. Next, the same procedure as in Evaluation Example I-1 was followed, except that the obtained toner particles (hereinafter referred to as toner 2A, toner 2B and toner 2C, respectively) were used, to yield developing agents 2A through 2C.

Each of the thus-obtained developing agents 2A through 2C was subjected to an actual picture taking test in the same manner as in Evaluation Example I-1.

The results are given in Table 5 below.

Evaluation Example I-3

Toner particles of 5 μm in average particle size were prepared in the same manner as in Evaluation Example I-1, except that the pigment-containing polymer particles obtained in Examples 3-A were used. Next, the same procedure as in Evaluation Example I-1 was followed, except that the obtained toner particles (hereinafter referred to as toner 3A) were used, to yield developing agent 3A.

The thus-obtained developing agent 3A was subjected to an actual picture taking test in the same manner as in Evaluation Example I-1.

The results are given in Table 5 below.

Evaluation Example I-4

Toner particles of 5 μm in average particle size were prepared in the same manner as in Evaluation Example I-1, except that the pigment-containing polymer particles obtained in Examples 4-A were used. Next, the same procedure as in Evaluation Example I-1 was followed, except that the obtained toner particles (hereinafter referred to as toner 4A) were used, to yield developing agent 4A.

The thus-obtained developing agent 4A was subjected to an actual picture taking test in the same manner as in Evaluation Example I-1.

The results are given in Table 5 below.

Comparative Evaluation Example I

Comparative toner particles of 5 μm in average particle size were prepared by the kneading milling method from a mixture of a binder resin consisting of a styrene-n-butyl acrylate copolymer (85:15 by weight) and carbon black (inorganic pigment) wherein the content of the inorganic pigment was the same as in toner 3A. After external additives were added in the same manner as above, the comparative toner particles were mixed with the above-described resin-coated carrier, to yield comparative developing agent 1. The obtained comparative developing agent 1 was subjected to an actual picture taking test in the same manner as in Evaluation Example I-1.

The results are given in Table 5 below.

TABLE 5

| Developing agent | Toner particles | Production of pigment-containing polymer particles (Example) | Resolution (lines/mm) | Fogging | Offset temperature (°C.) | Toner reflection density | Cleanability | Toner particle size distribution (number %) Initial | At fogging or after 50000 copies taken |
| --- | --- | --- | --- | --- | --- | --- | --- | --- | --- |
| Developing agent 1A | Toner 1A | 1-A | 20 | 90000 copies | 230 | ○ | 100000 copies | 2.3 | 2.6 |
| Developing agent 1B | Toner 1B | 1-B | 18 | 100000 copies | 240 | ○ | 90000 copies | 2.1 | 2.4 |
| Developing agent 1C | Toner 1C | 1-C | 16 | 80000 copies | 250 | ○ | 100000 copies | 2.6 | 3.1 |
| Developing agent 2A | Toner 2A | 2-A | 19 | 90000 copies | 190 | ○ | 100000 copies | 2.1 | 2.8 |
| Developing agent 2B | Toner 2B | 2-B | 18 | 100000 copies | 200 | ○ | 90000 copies | 2.6 | 3.0 |
| Developing agent 2C | Toner 2C | 2-C | 16 | 80000 copies | 220 | ○ | 100000 copies | 2.8 | 3.2 |
| Developing agent 3A | Toner 3A | 3-A | 20 | 90000 copies | 240 | ○ | 90000 copies | 1.8 | 2.0 |
| Developing agent 4A | Toner 4A | 4-A | 19 | 90000 copies | 200 | ○ | 90000 copies | 2.0 | 2.3 |
| Comparative developing agent 1 | Toner prepared by kneading milling method (carbon black) | | 8 | 50000 copies | 190 | X | 50000 copies | 5.7 | 11.3 |

From Table 5, it is seen that each of the developing agents containing toner particles from the pigment-containing polymer particles of the present invention (toners 1A-1C, toners 2A-2C, toners 3A and 4A) possesses excellent properties.

It is particularly notable that these toner particles have a sharp particle size distribution and show little changes over time in the particle size distribution and excellent durability.

Evaluation of Immunological Diagnostic Reagent Carrier

Evaluation Example II-1

Using the pigment-containing polymer particles (blue) obtained in Example 1-A, immunological diagnostic reagent particles 1A were prepared as follows:

To a dialytic cellulose bag of 1000 fractional molecular weight, the foregoing pigment-containing polymer particles were placed. After 24 hours of dialysis against pure water, the pigment-containing polymer particles were concentrated to a solid concentration of 5% using an ultrafiltration apparatus. After a buffer and sodium chloride were added, this concentrate was suspended in 0.1M PBS to yield a dispersion.

To the obtained dispersion, an anti-α-fetoprotein antibody (IgG fraction) was added, followed by 24 hours of physical adsorption at 4° C.

As a polymer solid, this dispersion was diluted with 0.2% 0.1M PBS (pH 7.2) to yield an immunological diagnostic reagent for AFP. Using 1000 mg/ml purified human α-fetoprotein (produced by Dako) as a mother liquor, serial dilutions were prepared at 1000 mg/ml, 500 mg/ml, 250 mg/ml, 125 mg/ml, 62.5 mg/ml, 31.25 mg/ml, 15.63 mg/ml and 7.81 mg/ml.

A 25 l portion of each AFP solution and 25 Bl of a latex reagent were mixed on a microplate, and the microplate was kept standing for 1 hour and then observed for coagulation. Using Serodia AFP mono (produced by Fujirebio Inc.) as a control, similar samples were assayed by a conventional method. The results are given in Table 6 below.

Evaluation Example II-2

Immunological diagnostic reagent particles 2A were prepared in the same manner as in Evaluation Example 1, except that the pigment-containing polymer particles (blue) obtained in Example 2-A were used, and were evaluated.

The results are given in Table 6 below.

Evaluation Example II-3

Immunological diagnostic reagent particles 3A were prepared in the same manner as in Evaluation Example 1, except that the pigment-containing polymer particles (black) obtained in Example 3-A were used, and were evaluated.

The results are given in Table 6 below.

Evaluation Example II-4

Immunological diagnostic reagent particles 4A were prepared in the same manner as in Evaluation Example 1, except that the pigment-containing polymer particles (black) obtained in Example 4-A were used, and were evaluated.

The results are given in Table 6 below.

TABLE 6

| Immunological diagnostic reagent particles | Production of pigment-containing polymer particles (Example) | AFP [mg/ml] | | | | | | | |
| --- | --- | --- | --- | --- | --- | --- | --- | --- | --- |
| | | 1000 | 500 | 250 | 125 | 62.5 | 31.25 | 15.63 | 7.81 |
| 1A | Example 1-A | + | + | + | + | + | + | + | − |
| 2A | Example 2-A | + | + | + | + | + | + | + | − |
| 3A | Example 3-A | + | + | + | + | + | + | + | − |
| 4A | Example 4-A | + | + | + | + | + | + | + | − |

TABLE 6-continued

| Immunological diagnostic reagent particles | Production of pigment-containing polymer particles (Example) | AFP [mg/ml] | | | | | | | |
|---|---|---|---|---|---|---|---|---|---|
| | | 1000 | 500 | 250 | 125 | 62.5 | 31.25 | 15.63 | 7.81 |
| Control test solution Serodia AFP mono | | ± | + | + | + | + | + | + | − |

Molecular Weight Control

Pigment-containing polymer particles were prepared in the same manner as in Examples 1-A, 2-A, 3-A and 4-A, respectively, except that the amount of potassium persulfate (polymerization initiator) added was step by step varied. With respect to each of the samples of pigment-containing polymer particles, the molecular weight of the polymer component was determined, using gel permeation chromatograph GPC (produced by Tosoh Corporation). The results are given in Table 7.

TABLE 7

| Example | Monomer composition | Polymerization initiator concentration (mol/l) | | | |
|---|---|---|---|---|---|
| | | 0.005 | 0.010 | 0.015 | 0.020 |
| Example 1-A | Hydrophobic monomer alone | 320,000 | 180,000 | 90,000 | 65,000 |
| Example 2-A | Hydrophilic monomer contained | 380,000 | 160,000 | 72,000 | 38,000 |
| Example 3-A | Hydrophobic monomer alone | 400,000 | 210,000 | 120,000 | 85,000 |
| Example 4-A | Hydrophilic monomer contained | 450,000 | 230,000 | 110,000 | 53,000 |

From Table 7, it is seen that the use of a monomer composition containing a hydrophilic monomer (Examples 2-A and 4-A) facilitates the molecular weight control of the polymer component and broadens the controllable range.

With by far smaller particle size than that of conventional pigment-containing polymer particles and excellent properties, the pigment-containing polymer particles of the present invention are preferably applicable to a variety of fields, including electrophotographic toners and immunological diagnostic reagent particles.

According to the method of the present invention, pigment-containing polymer particles of small particle size can be efficiently produced, since it is carried out while controlling the surfactant concentration in the aqueous system both at pigment dispersion and at aqueous separation polymerization reaction.

The electrophotographic toner of the present invention possesses excellent properties for a component of a developing agent. It is particularly notable that the electrophotographic toner of the invention has a sharp particle size distribution and shows little changes over time in particle size distribution and excellent durability.

What is claimed is:

1. A method of manufacturing a pigment containing polymer particle, comprising the steps of:
   dissolving a surface active agent in water to form a solution having a concentration higher than a critical micelle concentration;
   dispersing an organic or inorganic pigment into the solution to make a suspension wherein
   (a) an average diameter of organic pigment in the suspension is not more than 10 times an average diameter of a primary particle of the organic pigment; and
   (b) an average diameter of inorqanic pigment in the suspension is not more than 20 times an average diameter of a primary particle of the inorqanic pigment;
   diluting the suspension with water to form a diluted suspension having a concentration not higher than the critical micelle concentration; and
   adding a monomer comprising a hydrophobic monomer and a polymerization initiator into the diluted suspension to polymerize the monomer for forming the pigment-containing polymer particle.

2. The method of claim 1, wherein
the pigment is an organic pigment, and the monomer and the polymerization initiator satisfy the following formulas I and II:

$$0.001 \leq A \leq 0.03 \qquad \text{I}$$

$$0.004 \leq A/B \leq 0.10 \qquad \text{II}$$

wherein A is a concentration (mol per liter) of the polymerization initiator and B is a concentration (mol per liter) of the monomers.

3. The method of claim 2 wherein
the monomer further comprises a hydrophilic monomer, and a weight per cent of the hydrophilic monomer to the monomers is 0.1 to 15.0.

4. The method of claim 3, wherein
the hydrophilic monomer is a polar group substitutable monomer selected from the group consisting of a monomer containing a carboxyl group, a monomer containing a sulfo group, a monomer containing a primary amine group, a monomer containing a secondary amine group, a monomer containing a tertiary amine group, and a monomer containing a quaternary ammonium salt group, all capable of introducing the polar group to the side chain of a polymer therefrom.

5. The method of claim 1, wherein
the pigment is an inorganic pigment, and the monomer and the polymerization initiator satisfy the following formulas I and II:

$$0.001 \leq A \leq 0.03 \qquad \text{I}$$

$$0.004 \leq A/B \leq 0.10 \qquad \text{II}$$

wherein A is a concentration (mol per liter) of the polymerization initiator and B is a concentration (mol per liter) of the monomers.

6. The method of claim 5, wherein
the monomer further comprising a hydrophilic monomer, and a weight per cent of the hydrophilic monomer to the monomers is 0.1 to 15.0.

7. The method of claim 6, wherein
the hydrophilic monomer is a polar group substitutable monomer selected from the group consisting of a monomer containing a carboxyl group, a monomer containing a sulfo group, a monomer containing a primary amine group, a monomer containing a secondary amine group, a monomer containing a tertiary amine group, and a monomer containing a quaternary ammonium salt group, all capable of introducing the polar group to the side chain of a polymer therefrom.

8. The method of claim 5, wherein
the inorganic pigment is selected from the group consisting of a carbon black, a ferrite group, and a magnetite group.

9. The method of claim 5, wherein
the inorganic pigment is processed with a surface improver.

10. A method of manufacturing an immunological diagnostic reagent carrier, comprising the steps of:
dissolving a surface active agent in water to form a solution having a concentration higher than a critical micelle concentration;
dispersing an orqanic or inorganic pigment into the solution to make a suspension, wherein
  (a) an average diameter of organic pigment in the suspension is not more than 10 times an average diameter of a primary particle of the organic pigment; and
  (b) an average diameter of inorqanic pigment in the suspension is not more than 20 times an average diameter of a primary particle of the inorganic pigment;
diluting the suspension with water to form a diluted suspension having a concentration not higher than the critical micelle concentration; and
adding a monomer comprising a hydrophobic monomer and a polymerization initiator into the diluted suspension to polymerize the monomer for forming pigment-containing polymer particles as the immunological diagnostic reagent carrier.

11. The method of claim 10, wherein
the pigment is an organic pigment, and the monomer and the polymerization initiator satisfy the following formulas I and II:

$$0.001 \leq A \leq 0.03 \quad \text{I}$$

$$0.004 \leq A/B \leq 0.10 \quad \text{II}$$

wherein A is a concentration (mol per liter) of the polymerization initiator and B is a concentration (mol per liter) of the monomers.

12. The method of claim 11, wherein the monomer further comprises a hydrophilic monomer, and a weight per cent of the hydrophilic monomer to the monomers is 0.1 to 15.0.

13. The method of claim 12, wherein
the hydrophilic monomer is a polar group substitutable monomer selected from the group consisting of a monomer containing a carboxyt group, a monomer containing a sulfo group, a monomer containing a primary amine group, a monomer containing a secondary amine group, a monomer containing a tertiary amine group, and a monomer containing a quaternary ammonium salt group, all capable of introducing the polar group to the side chain of a polymer therefrom.

14. The method of claim 10, wherein
the pigment is an inorganic pigment, and the monomer and the polymerization initiator satisfy the following formulas I and II:

$$0.001 \leq A \leq 0.03 \quad \text{I}$$

$$0.004 \leq A/B \leq 0.10 \quad \text{II}$$

wherein A is a concentration (mol per liter) of the polymerization initiator and B is a concentration (mol per liter) of the monomers.

15. The method of claim 14, wherein
the monomer further comprising a hydrophilic monomer, and a weight per cent of the hydrophilic monomer to the monomers is 0.1 to 15.0.

16. The method of claim 15, wherein
the hydrophilic monomer is a polar group substitutable monomer selected from the group consisting of a monomer containing a carboxyl group, a monomer containing a sulfo group, a monomer containing a primary amine group, a monomer containing a secondary amine group, a monomer containing a tertiary amine group, and a monomer containing a quaternary ammonium salt group, all capable of introducing the polar group to the side chain of a polymer therefrom.

17. The method of claim 14, wherein
the inorganic pigment is selected from the group consisting of a carbon black, a ferrite group, and a magnetite group.

18. The method of claim 14, wherein
the inorganic pigment is processed with a surface improver.

19. A method of manufacturing a toner for electrophotography, comprising the steps of:
dissolving a surface active agent in water to form a solution having a concentration higher than a critical micelle concentration;
dispersing an organic or inorganic pigment into the solution to make a suspension, wherein
  (a) an average diameter of organic pigment in the suspension is not more than 10 times an averaqe diameter of a primary particle of the orqanic pigment; and
  (b) an average diameter of inorganic pigment in the suspension is not more than 20 times an average diameter of a primary particle of the inorganic pigment;
diluting the suspension with water to form a diluted suspension having a concentration not higher than the critical micelle concentration; and
adding a monomer comprising a hydrophobic monomer and a polymerization initiator into the diluted suspension to polymerize the monomer for forming pigment-containing polymer particles; and
coagulating or fusing the pigment-containing polymer particles to form the toner for electrophotography.

20. The method of claim 19, wherein
the pigment is an organic pigment, and the monomer and the polymerization initiator satisfy the following formulas I and II:

$$0.001 \leq A \leq 0.03 \quad \text{I}$$

$$0.004 \leq A/B \leq 0.10 \quad \text{II}$$

wherein A is a concentration (mol per liter) of the polymerization initiator and B is a concentration (mol per liter) of the monomers.

21. The method of claim 20, wherein the monomer further comprising a hydrophilic monomer, and a weight per cent of the hydrophilic monomer to the monomers is 0.1 to 15.0.

22. The method of claim 21, wherein
the hydrophilic monomer is a polar group substitutable monomer selected from the group consisting of a monomer containing a carboxyl group, a monomer containing a sulfo group, a monomer containing a primary amine group, a monomer containing a secondary amine group, a monomer containing a tertiary amine group, and a monomer containing a quaternary ammonium salt group, all capable of introducing the polar group to the side chain of a polymer therefrom.

23. The method of claim 19, wherein
the pigment is an inorganic pigment, and the monomer and the polymerization initiator satisfy the following formulas I and II:

$$0.001 \leqq A \leqq 0.03 \qquad \text{I}$$

$$0.004 \leqq A/B \leqq 0.10 \qquad \text{II}$$

wherein A is a concentration (mol per liter) of the polymerization initiator and B is a concentration (mol per liter) of the monomers.

24. The method of claim 23 wherein
the monomer further comprising a hydrophilic monomer, and a weight per cent of the hydrophilic monomer to the monomers is 0.1 to 15.0.

25. The method of claim 24, wherein
the hydrophilic monomer is a polar group substitutable monomer selected from the group consisting of a monomer containing a carboxyl group, a monomer containing a sulfo group, a monomer containing a primary amine group, a monomer containing a secondary amine group, a monomer containing a tertiary amine group, and a monomer containing a quaternary ammonium salt group, all capable of introducing the polar group to the side chain of a polymer therefrom.

26. The method of claim 23, wherein
the inorganic pigment is selected from the group consisting of a carbon black, a ferrite group, and a magnetite group.

27. The method of claim 23, wherein
the inorganic pigment is processed with a surface improver.

* * * * *

UNITED STATES PATENT AND TRADEMARK OFFICE
CERTIFICATE OF CORRECTION

PATENT NO. : 5,415,964

DATED : May 16, 1995

INVENTOR(S) : Kenji HAYASHI et al

Page 1 of 2

It is certified that error appears in the above-indentified patent and that said Letters Patent is hereby corrected as shown below:

Claim 1, Column 25, Line 66, after "suspension" insert --,--.

Claim 1, Column 26, Line 11, change "inorqanic" to --inorganic--.

Claim 1, Column 26, Line 13, change "inorqanic" to --inorganic--.

Claim 10, Column 27, Line 19, change "orqanic" to --organic--.

Claim 10, Column 27, Line 25, change "inorqanic" to --inorganic--.

Claim 13, Column 27, Line 56, change "carboxyt" to --carboxyl--.

UNITED STATES PATENT AND TRADEMARK OFFICE
CERTIFICATE OF CORRECTION

PATENT NO. : 5,415,964
DATED : May 16, 1995
INVENTOR(S) : Kenji HAYASHI et al

It is certified that error appears in the above-indentified patent and that said Letters Patent is hereby corrected as shown below:

Claim 19, Column 28, Line 39, change "averaqe" to --average--.

Claim 19, Column 28, Line 40, change "orqanic" to --organic--.

Claim 20, Column 28, Formula I, above Formula I, insert a space.

Claim 23, Column 29, Formula I, above Formula I, insert a space.

Signed and Sealed this

Twenty-fourth Day of October, 1995

Attest:

BRUCE LEHMAN

*Attesting Officer*   *Commissioner of Patents and Trademarks*